Figure 1:
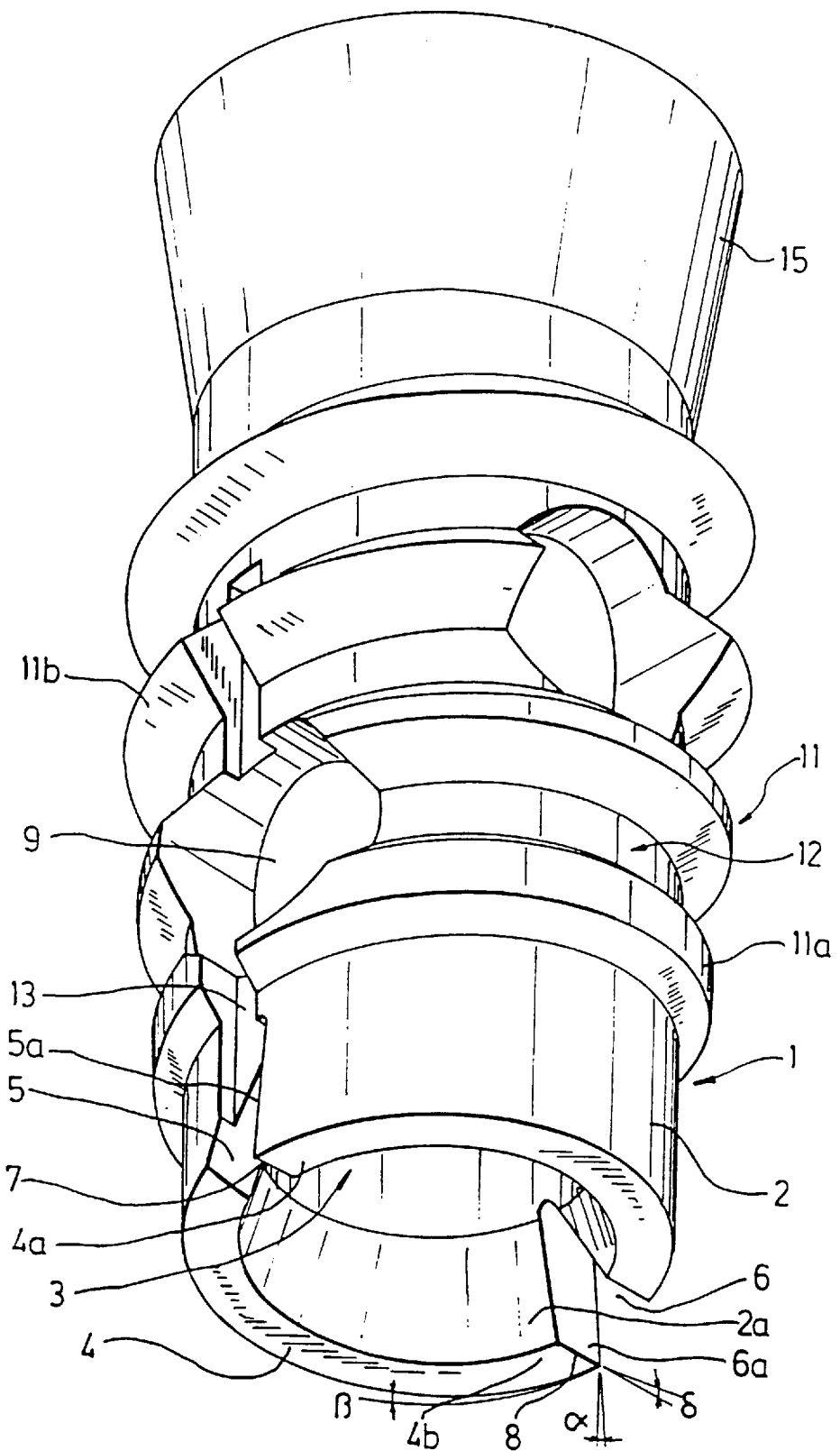

United States Patent [19]
Guedj

[11] Patent Number: 5,871,356
[45] Date of Patent: Feb. 16, 1999

[54] DENTAL IMPLANTS AND BORING INSTRUMENTS FOR IMPLANTING

[76] Inventor: Léon Guedj, 66 chemin Michoun, 31500 Toulouse, France

[21] Appl. No.: 894,383
[22] PCT Filed: May 23, 1996
[86] PCT No.: PCT/FR96/00771
 § 371 Date: Nov. 26, 1997
 § 102(e) Date: Nov. 26, 1997
[87] PCT Pub. No.: WO96/38098
 PCT Pub. Date: Dec. 5, 1996

[30] Foreign Application Priority Data

May 30, 1995 [FR] France .................................. 95 06627

[51] Int. Cl.$^6$ ...................................................... A61C 8/00
[52] U.S. Cl. .......................... 433/174; 433/165; 433/173
[58] Field of Search .................................... 433/174, 173, 433/172, 165

[56] References Cited

U.S. PATENT DOCUMENTS

| | | | |
|---|---|---|---|
| 4,185,383 | 1/1980 | Heimke et al. | 433/173 |
| 4,738,616 | 4/1988 | Reynaud | 433/165 |
| 5,259,398 | 11/1993 | Vrespa | 433/174 |
| 5,366,374 | 11/1994 | Vlassis | 433/173 |
| 5,571,017 | 11/1996 | Niznick | 433/173 |
| 5,642,996 | 7/1997 | Mochida et al. | 433/174 |

FOREIGN PATENT DOCUMENTS

| | | |
|---|---|---|
| 0 412 845 | 2/1991 | European Pat. Off. . |
| 2 571 607 | 8/1986 | France . |
| 2 610 820 | 8/1988 | France . |
| 2 119 258 | 11/1983 | United Kingdom . |
| WO 94/22389 | 10/1994 | WIPO . |

*Primary Examiner*—John J. Wilson
*Attorney, Agent, or Firm*—Young & Thompson

[57] ABSTRACT

A surgical equipment for implanting dental implants has a boring instrument and an endo-osseous dental implant. The endo-osseous dental implant has a tubular distal section with a cylindrical wall that turns around an axis, and is provided with an outer thread and delimits an inner bone material holding volume. Its distal end having a thickness "e" which forms a ring-shaped transverse base with an inner diameter "d" and an outer diameter "d+2e". The cylindrical wall has at least one distal indentation that forms a front cutting edge at the ring-shaped base. Also disclosed is a boring instrument with a stepped drill having a distal section with a diameter between "d" and "d+2e" and a proximal section with a diameter of at least "d+2e" but smaller than the outer diameter of the thread of the dental implant.

15 Claims, 5 Drawing Sheets

DENTAL IMPLANTS AND BORING INSTRUMENTS FOR IMPLANTING

The invention relates to surgical equipment for dental implantology and extends to component parts of this equipment, consisting of an endosseous dental implant and of a drilling instrument.

A standard procedure used for the placement of implants in the dental field consists mainly of first generating an implant cavity of dimensions adapted to those of the implant by means of drills of increasing diameter, of threading this cavity with a screw thread and of screwing said implant in said cavity. In a second phase, after a period of four to six months called immobilization during which cicatrization of the bone occurs, a pillar or stump designed to be used as support for the prosthesis is united with the implant.

Since one of the conditions of success in implantology is the creation of intimate contact between the bone and the implant immediately after surgery, one of the difficult phases of this procedure consists of constructing an implantology cavity perfectly calibrated to the dimensions of the implant.

Now, in practice, in spite of the use of perfectly calibrated instrumentation and the meticulousness of the practitioners, it proves difficult to construct a cavity perfectly adapted to the dimensions of the implant and a source of failure in implantology hence results from a poor immediate immobilization of said implant.

In an attempt to remedy this disadvantage, a novel procedure has consisted in constructing self-screw threaded implants such as for example that described in patent EP 237.505 which comprises three longitudinal cutting edges arranged towards the distal end of said implant, each defining an external cavity arranged so as to make it possible to collect the bone shavings during the placement.

Owing to their self-screw threading character, such implants make it possible to obtain a better intimate contact with the bone and consequently to increase the primary stability of said implants. However, in spite of the presence of the external cavities for collecting the bone shavings, such implants may cause compression of the bone removed which results in a necrosis of the bone cells. Furthermore, the operating procedure for the placement of such an implant proves to be relatively complex and difficult. In fact, this placement makes it necessary to carry out in particular a predrilling, a first drilling with for example a 2 mm drill, another predrilling with the aid of an instrument comprising a 2 mm diameter blunt tip followed by a 3 mm diameter sharp-edged part, a second drilling by means of a 3 mm drill, and a widening with the aid of a so-called "counter-sink" special drill. In practice, the operating time required for the surgical placement of an implant proves to be considerable. In addition, the increase in the number of operations to be performed proves to be a not inappreciable source of potential errors concerning in particular the geometry of the cavity.

The present invention aims to remedy all of the disadvantages previously mentioned concerning the surgical procedures for the placement of dental implants and its essential objective is to provide surgical equipment which, on the one hand, makes it possible to appreciably simplify the operating procedure for the placement of implants and, on the other, to achieve an intimate bone/implant contact at the time of surgery.

For this purpose, the invention relates to surgical equipment consisting of a drilling instrument and an endosseous dental implant according to which the endosseous dental implant consists of:

a proximal section comprising a device for the attachment of a placement tool for said implant, and a threaded upper aperature capable of making possible the insertion of a stump, a distal tubular section comprising a cylindrical wall of rotation about an axis defining a internal storage volume of the osseous tissue, and possessing a distal end of thickness "e" forming an annular transverse base of internal diameter "d" and of external diameter "d+2e", said cylindrical wall comprising at least one distal indentation forming a cutting front edge at the annular base, defined by said annular base and one of the faces of said indentation shaped so as to define a relief face and a cutting face, an external threading comprising at least one distal cutting edge, arranged on said dental implant and starting at a distance from the annular base of the distal section, the drilling instrument comprises a stepped drill having a distal section of diameter included between "d" and "d+2e" and a proximal section of diameter at least equal to "d+2e" and less than the external diameter of the threading of the dental implant.

For the purpose of inserting an implant such surgical equipment simply makes it necessary to construct an implant precavity by means of the stepped drill in conformity with the invention, the distal part of which is adapted to form a bore of smaller diameter than the external diameter of the distal section and the upper section of which is adapted to form a bore of diameter at least equal to this diameter in the very dense and hard cortical part of the bone. It should be noted that this insertion may, however, first require the carrying out of a predrilling by means of a standard 2 mm drill, for example.

Once this implant pre-cavity has been formed in one or two operations only, the implant can be inserted directly, since it has been designed to generate on insertion a bore in the lower portion of the implant pre-cavity drilled initially by the distal section of the stepped drill, during which the osseous tissue removed by each cutting front edge is stored within the distal section of said implant, on the one hand, and, on the other hand, a self-screw threading.

The operating procedure for the placement of the implants conforming to the invention thus proves to be very simple and very quick because it only requires one or two major operations prior to the insertion of the implants.

Furthermore, from its design, the dental implant according to the invention, which has a dual bore action with storage of the osseous tissue removed and self-screw threading, makes it possible to obtain both an optimal intimate contact with the bone and a primary stability without causing compression of the osseous tissue removed which would risk causing necrosis of the bone cells. As a result it first makes it possible to diminish the risks of failure of the implantation operation. Furthermore, it causes a rapid osteointegration which allows a reduction of the immobilization time.

According to another characteristic of the invention, the proximal section of the dental implant comprises a widened upper end portion exhibiting a truncated cone shape, and the stepped drill comprises an upper section, extending the proximal section of truncated cone shape adapted to that of the dental implant.

This truncated cone shape of the upper section of the drill makes it possible to create a widening of the end of the implant precavity possessing a shape identical with that of the upper portion of the dental implant, which advantageously forms an aperture for the alignment of said implant during its insertion.

Furthermore, once the dental implant has been inserted, such a widening makes it possible to obtain an intimate upper portion/bone contact of said implant which is a guarantee against any bacterial penetration.

According to another characteristic of the invention, the cylindrical wall of the distal section of the dental implant has an skewed distal end forming an annular base inclined transversally in the direction of the internal volume defined by said peripheral wall.

This skewed form of the annular base comprising the cutting front edge has the advantage of guiding the bone shavings in the direction of the internal storage volume of the dental implant.

For the same purpose, the internal storage volume advantageously possesses, starting from the annular base, a truncated cone-shaped portion widening in the direction of said annular base.

In addition, in order to enhance the efficacy of the frontal shaving of the dental implant the cylindrical wall of the distal section advantageously comprises two indentations arranged symmetrically to one another with respect to the longitudinal axis of said dental implant, the annular base possessing between each of the said indentations a helicoidal shape forming a relief face for each cutting front edge.

According to another characteristic of the invention the cylindrical wall of the distal section comprises at least one longitudinal indentation notch arranged on the external face of said wall, of transverse section adapted to form a longitudinal cutting edge.

Each of the indentation notches hence possesses a longitudinal cutting edge for example straight or helicoidal which makes it possible to initiate the action of self-screw threading of the dental implant. In addition, such indentation notches form an external chamber which makes it possible to collect the bone shavings resulting from this self-screw threading.

Each of these indentation notches may be extended in addition either from the annular base of the cylindrical wall in an angular position displaced with respect to each indentation, or in the prolongation of one of said indentations.

Moreover, according to another characteristic of the invention, the external threading first possesses, from its distal end, threads of trapezoidal section extended by threads of triangular cross-section, forming a threading of progressive cross-section.

Furthermore, the threads of this external threading are preferably spaced so as to define grooves of trapezoidal crosssection.

These external threading forms in fact make it possible, on the one hand, to obtain a progressive self-screw threading and, on the other hand, to cut away a minimal amount of osseous tissue while guaranteeing perfect retention of the implant in the implant cavity as a result of the spacing of the threads.

According to another characteristic of the invention, the cylindrical wall of the distal section comprises circular secondary wedging apertures the axis of which is non-intersecting with respect to the axis of revolution of said implant.

In addition to their standard function of secondary wedging, such apertures, owing to their eccentric position with respect to a diametral plane of the implant, possess cutting edges complementary to the passage of the threads of the external threading making it possible to complete the bore of the implant cavity.

Furthermore, the axis of each of these secondary wedging apertures is advantageously inclined in the direction of the proximal section of said dental implant, so as to cause the shavings to enter naturally into the internal storage volume.

Moreover, concerning the device for attachment to the proximal section of the dental implant, this latter may advantageously consist in a standard manner of a head of polygonal section.

According to a variant of the embodiment, the upper aperture consists of a threaded mold of a shape designed to serve also as reserve hole aperture adapted to be attached to a tool for the insertion of said implant.

This arrangement which consists of bringing together at the level of a unique portion of the proximal section two zones which are at present the prolongation of one another, in fact makes it possible for the same length of implant to increase the internal storage volume of this latter.

The invention extends to an endosseous dental implant comprising:
    a proximal section comprising a device for attachment to an insertion tool for said implant, and a screw threaded upper aperture capable of making possible the insertion of a stump,
    a distal tubular section comprising a cylindrical wall of rotation about an axis defining an internal storage volume for the osseous tissue and having a distal end of thickness "e" forming an annular transversal base of internal diameter "d" and external diameter "d+e", said cylindrical wall comprising at least one distal indentation forming a cutting front edge at the annular base, defined by said annular base and one of the faces of said indentation shaped so as to define respectively a relief face and a cutting face,
    an external screw threading comprising at least one distal cutting edge, arranged on said dental implant and starting at a distance from the annular base of the distal section.

It also extends to a drill for the generation of an implant cavity designed for the insertion of a bone implant, comprising a distal section of predefined diameter and a proximal section of diameter greater than that of the distal section.

Figure 2:
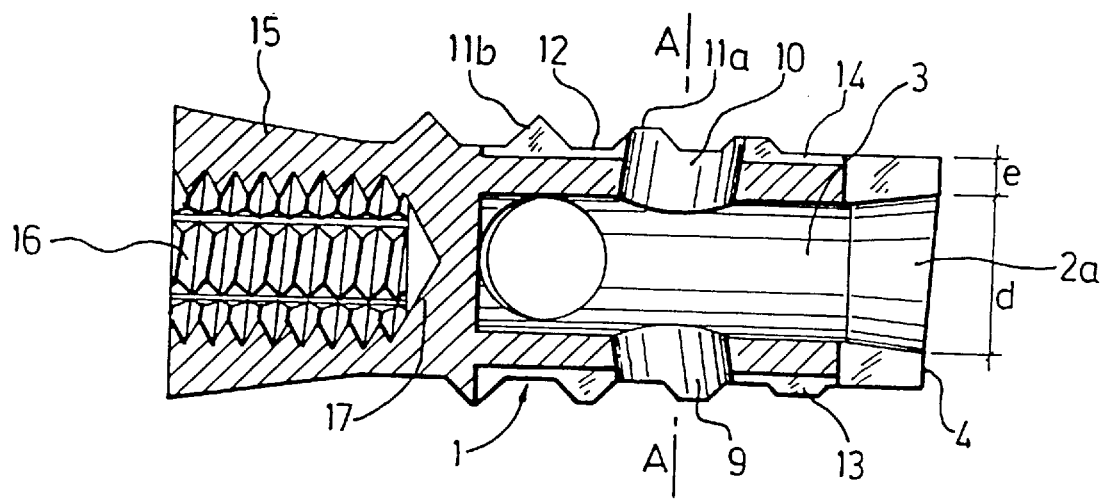
Figure 3:
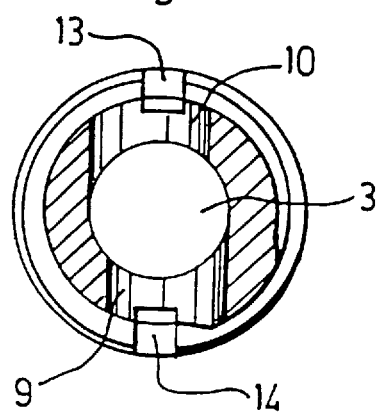
Figure 4:
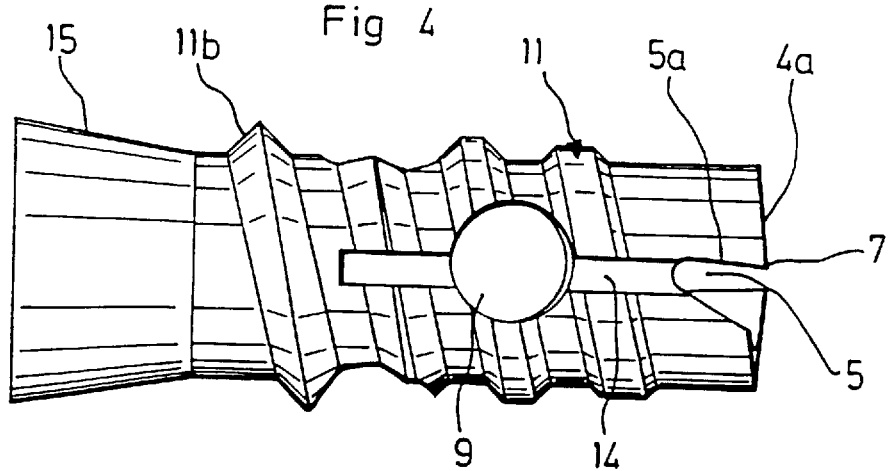
Figure 5:
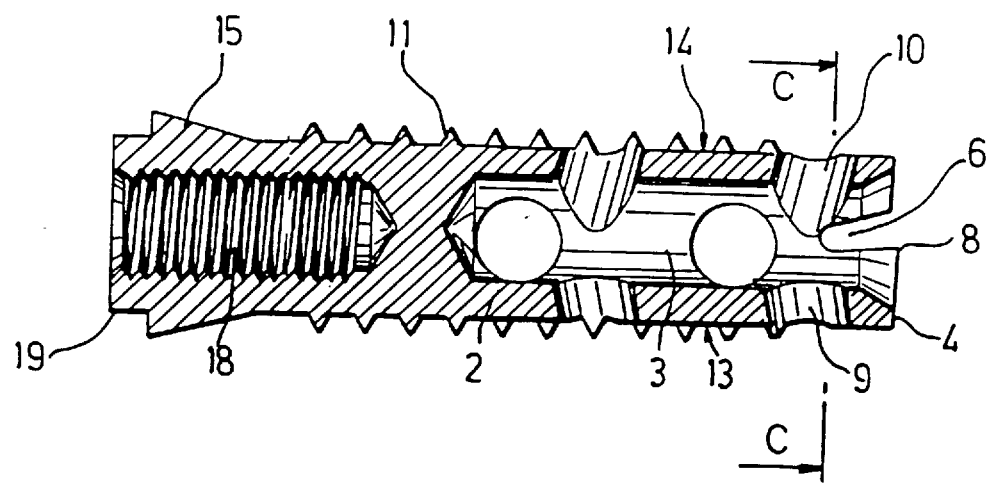
Figure 6:
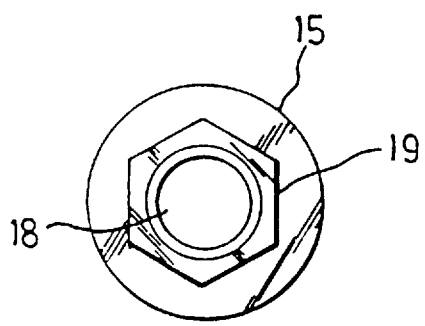
Figure 7:
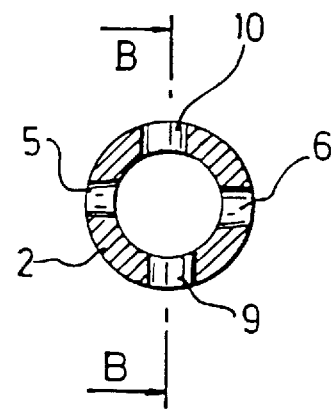
Figure 8:
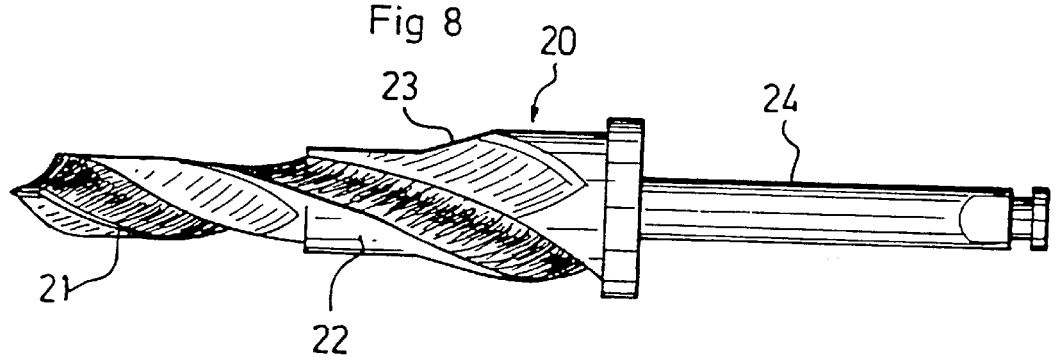
Figure 9:
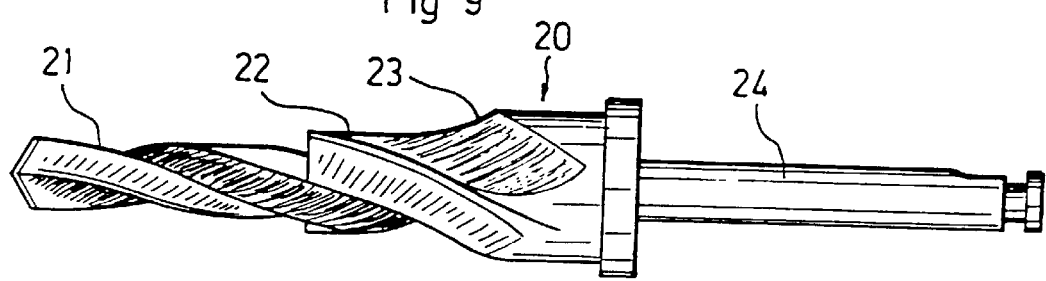

Other characteristics, aims and advantages of the invention will become apparent from the detailed description which follows with reference to the appended drawings which present two preferred embodiments of it as non-limiting examples. On these drawings which form an integral part of the invention:

FIG. 1 is a perspective view of a first embodiment of a dental implant in conformity with the invention, FIG. 2 is an axial longitudinal section of it, FIG. 3 is a transverse section of it through a plane A, FIG. 4 is a longitudinal view in profile of it, FIG. 5 is a longitudinal section through an axial plane B of a second embodiment of a dental implant conforming to the invention, FIG. 6 is a plan view of it FIG. 7 is a transverse section through a plane C FIGS. 8 and 9 are two longitudinal views of a stepped drill conforming to the invention at 90° to each other, and FIGS. 10a to 10d are schematic views representing the different phases of the insertion of an implant conforming to the invention.

The dental implants presented in the Figures show the feature exhibiting two cutting front edges which make it possible to generate a calibrated bore during which the osseous tissue is stored within these implants, and an external threading making it possible to achieve a self-screw threading.

In the first instance, the dental implant shown in FIGS. 1 to 4 consists of a distal tubular section 1 comprising a cylindrical wall 2 of rotation about an axis defining an internal storage volume 3 for the osseous tissue.

This cylindrical wall 2 comprises an internally chamfered distal end section 2a conferring a flared truncated cone shape on the lower portion of the internal storage volume 3, and forming a helicoidal annular transverse base 4 of internal diameter "d" and external diameter "d+2e".

This cylindrical wall 2 also comprises two distal indentations 5, 6 arranged symetrically to each other with respect to the longitudinal axis of the dental implant each forming a cutting front edge at the annular transverse base 4.

In addition, in order to arrange these cutting front edges, each of the indentations 5, 6 forms a cutting face 5a, 6a inclined at an angle α of the order of 4 to 10 degrees with respect to the longitudinal axis of the implant whereas the annular transverse base 4 exhibits, between each of the indentations, a helicoidal shape forming for each of said front cutting faces 7, 8 a relief face 4a, 4b inclined at an angle β of the order of 4 to 10 degrees with respect to a transverse plane.

Furthermore, the annular transverse base 4 is skewed so as to be inclined transversally in the direction of the internal storage volume 3 at an angle δ of the order of 4 to 10 degrees with respect to a radial axis.

In addition apertures such as 9, 10 of secondary wedging are drilled into the cylindrical wall 2 and arranged in pairs symmetrically opposite one another with respect to the longitudinal axis of the dental implant, and the axis of symmetry of which is non-intersecting with said longitudinal axis so that each of said apertures exhibits a supplementary cutting edge.

These apertures 9, 10, the even number of which is a function of the length of the dental implant are distributed pairwise over that length of the distal section 1 situated above the indentations 5,6 and are arranged such that each pair of apertures 5,6 is displaced by 90 degrees with respect to the neighboring pair.

In addition, the axis of each of these apertures 9, 10 is inclined in a direction opposite to the annular base 4, so as to cause the bone shavings to enter naturally into the internal storage volume 3.

The cylindrical wall 2 is moreover equipped with an external thread 11, the distal end of which starts above the indentations 5,6 which, with increasing height, have a cross-section progressing from a trapezoidal shape for the first threads 11a and a triangular shape for the last threads 11b.

In addition, these threads 11a, 11b are spaced so as to define grooves 12 of trapezoidal cross-section in proportion with the step and the height of the thread.

The peripheral wall 2 comprises, finally, two indentation notches 13, 14 of rectangular cross-section in the example, arranged longitudinally in the prolongation of each of the indentations 5, 6 and each designed to exhibit a longitudinal cutting edge which makes it possible to initiate the self-screw-threading action of the external threading 11.

These indentation notches 13, 14 extend in addition over the portion of length of the distal section 1 provided with an external thread 11 of "truncated" section destined to accomplish the self-screw-threading.

The dental implant shown in FIGS. 1 to 4 also comprises a proximal section 15 of widened truncated cone shape, pierced by an axial mold 16 of less deep than said proximal section such that the bottom of said mold is separated from the internal storage volume 3 by a thickness of material 17.

This mold 16 has the shape of a star, for example of the type of mold known by the designation "TORQ", inscribed in a circle and whose areas of material forming the branches and defined by the circumscribing circle are screw threaded.

In this manner, this mold 16 has a shape adapted to cooperate with a star-shaped tool coupled for the purpose of inserting the implant, and forms an upper threaded aperture capable of making possible the insertion of a stump.

As regards the dental implant shown in FIGS. 5 to 7, it consists of a distal structural section identical with that of the implant described above (for the purposes of simplification the same reference numbers will be used to designate similar elements of the two variants of the implant).

This dental implant hence consists principally of: a cylindrical wall 2 defining an internal storage volume 3, the distal end of which has two indentations 5,6, and forms a helicoidal annular base 4 fitted with two cutting front edges such as 8 at said indentations, apertures of secondary wedging 9, 10 (8 in the example given), an external threading 11 and two indentation notches 13, 14.

This dental implant also comprises a proximal section 15 in the shape of a flared truncated cone. On the other hand, instead of the mold 16, this proximal section 15 comprises, like some current implants, a threaded axial bore 18 destined for the insertion of a stump, and a hexagonal-shaped head 19.

As an example, the dimensions of the dental implant such as that described above may be the following, given as an indication:

total length of the order of 17 mm,
length of the distal section 1 about 13 mm,
internal diameter "d" of the annular base 4: 2.6 mm,
external diameter "d+2e" of the annular base: 3.4 mm
external diameter of the thread 11: 4 mm
maximal external diameter of the proximal section 15: 4.1 mm.

As shown in FIGS. 8, 9, the drill 20 designed to form the implant pre-cavity for the insertion of a dental implant conforming to the invention is a helicoidal drill comprising two helicoidal grooves, and consisting of a distal section 21 of diameter included between "d" and "d+2e", a proximal section 22 of diameter "d+2e", and an upper truncated cone-shaped section 23 conjugated with the proximal head 15 of the implants, prolonged in a standard manner by a handle 24 for attachment to a tool.

As an example, for a dental implant whose dimensions correspond to those mentioned above, such a drill will have a distal section 21 of 2.8 mm diameter and a proximal section 22 of 3.4 mm diameter.

FIG. 10 represents the implant pre-cavity 25 obtained by means of such a drill as 20, after a possible preliminary carrying out of a pre-drilling for example by means of a drill of 2 mm diameter, comprising an upper widening 25a, an upper bore 25b of 3.4 mm diameter in the cortical part of the bone, and in the extension of this latter a smaller bore 25c of 2.8 mm diameter.

Figure 10A:
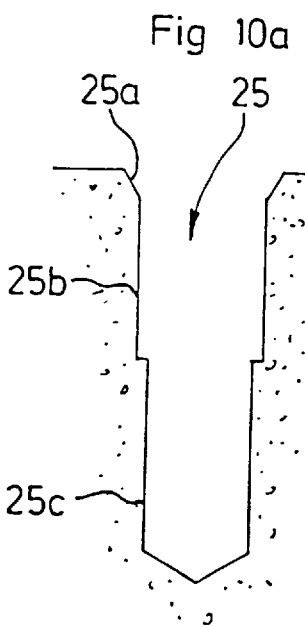
Figure 10B:
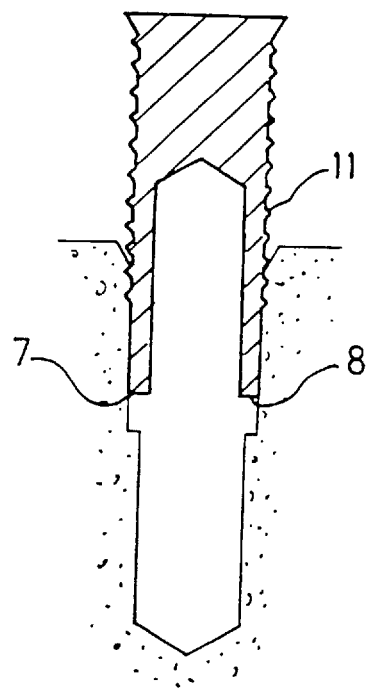
Figure 10C:
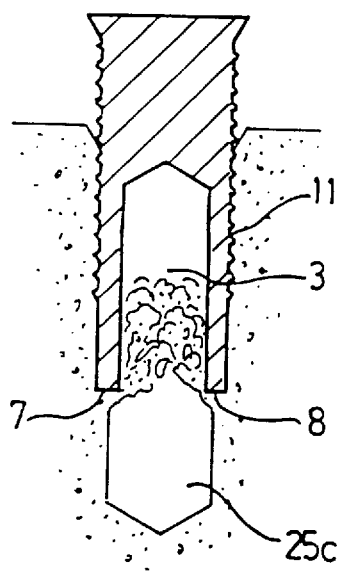
Figure 10D:
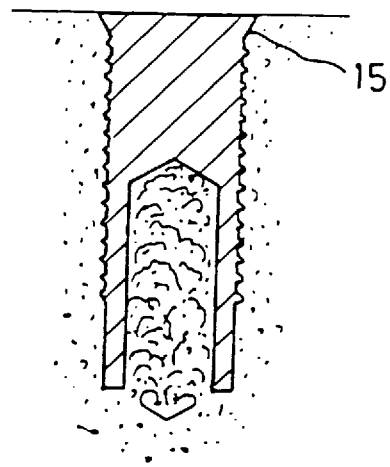

During the insertion of the implant and as shown in FIGS. 10b to 10d, this latter has a boring action of the smaller bore 25c, performed as a result of the presence of the cutting front edges 7,8, and during which the osseous tissue removed is stored within the internal volume 3.

Furthermore, this implant has a self-threading action initiated by the longitudinal cutting edge of the indentation notches 13, 14 and carried out by the external threading 11.

Moreover, once inserted, the proximal section 15 of the implant is accommodated in the wide opening 25a in intimate contact with the bone.

The design of this implant, with the construction of an internal storage volume 3 adapted to accommodate the osseous tissue removed and whose dimensions for this purpose may be easily defined (by taking into account, if need be, the storage volume of the apertures of secondary wedging 9, 10 and of the indentation notches 13, 14), makes it possible to obtain both optimal intimate contact with the bone and primary stability without causing compression of the osseous tissue removed.

I claim:

1. Surgical equipment for dental implantology comprising a drilling instrument and an endosseous dental implant, wherein:

the endosseous dental implant consists of:

a proximal section (15) comprising means for attachment (16; 19) to a placement tool for said implant and a threaded upper aperture (16; 18) for the insertion of a stump, a tubular distal section (1) comprising a cylindrical wall (2) defining an internal storage volume (3) for osseous tissue and having a distal end of thickness "e" forming an annular transverse base (4) of internal diameter "d" and external diameter "d+2e", said cylindrical wall comprising at least one distal indentation (5, 6) forming a cutting front edge (7, 8) at the annular base (4), defined by said annular base and a face (5a, 6a) of said indentation shaped so as to define a relief face (4a, 4b) and a cutting face (5a, 6a), an external thread (11) comprising at least one distal cutting edge (13, 14) arranged on said dental implant and starting at a distance from the annular base (4) of the distal section (1), the drilling instrument consists of a stepped drill (20) possessing a distal section (21) of diameter included between "d" and "d+2e" and a proximal section (22) of diameter at least equal to "d+2e" and less than an external thread diameter (11) of the dental implant.

2. Surgical equipment according to claim 1, wherein:

the proximal section (15) of the dental implant comprises a truncated conical widened upper end portion, the stepped drill (20) comprises a truncated conical upper section (23), forming an extension of the proximal section (22) and coaxial with said widened upper end portion.

3. Endosseous dental implant, which comprises:

a proximal section (15) comprising means for attachment (16; 19) to a placement tool for said implant, and a threaded upper aperture (16; 18) for the insertion of a stump, a tubular distal section (1) comprising a cylindrical wall (2) defining an internal storage volume (3) for osseous tissue and having a distal end of thickness "e" forming an annular transverse base (4) of internal diameter "d" and external diameter "d+2e", said cylindrical wall comprising at least one distal indentation (5, 6) forming a cutting front edge (7, 8) at the annular base (4), defined by said annular base and one of the shaped faces (5a, 6a) of said indentation shaped so as to define a relief face (4a, 4b) and a cutting face (5a, 6a), an external thread (11) comprising at least one distal cutting edge (13, 14) arranged on said dental implant and starting at a distance from the annular base (4) of the distal section (1).

4. Dental implant according to claim 3, which further comprises a truncated cone-shaped upper end portion (15).

5. Dental implant according to claim 3, wherein the cylindrical wall (2) of the distal section (1) possesses a skewed distal end forming an annular base (4) transversally inclined in the direction of the internal volume (3) defined by said peripheral wall.

6. Dental implant according to claim 3, wherein the internal storage volume (3) possesses starting from the annular base (4), a truncated cone-shaped volume portion (2a) widening in the direction of said annular base.

7. Dental implant according to claim 3, wherein the cylindrical wall (2) of the distal section (1) comprises two indentations (5, 6) arranged symmetrically to each other with respect to a longitudinal axis of said dental implant, the annular base (4) between each of said indentations having a helicoidal shape forming a relief face (4a, 4b) for each cutting front edge (7, 8).

8. Dental implant according to claim 3, wherein the cylindrical wall (2) of the distal section (1) comprises at least one longitudinal indentation notch (13, 14) arranged on a external face of said wall, of transverse section adapted to form a longitudinal cutting edge.

9. Dental implant according to claim 8, wherein each indentation notch (13, 14) extends from the annular base (4) of the cylindrical wall (2) and is displaced at an angle to each indentation (5, 6).

10. Dental implant according to claim 8, wherein each indentation notch (13, 14) extends in prolongation of an indentation (5, 6).

11. Dental implant according to claim 3, wherein the external thread (11) possesses from its distal end initial threads (11a) of trapezoidal cross-section extended by threads (11b) of triangular cross-section, forming a screw thread of progressive cross-section.

12. Dental implant according to claim 11, wherein the threads (11a, 11b) of the external threading (11) are spaced so as to define grooves (12) of trapezoidal cross-section.

13. Dental implant according to claim 3, wherein the cylindrical wall (2) of the distal section (1) comprises circular secondary wedging apertures (9, 10) having an axis which is non-intersecting with respect to an axis of rotation of said implant.

14. Dental implant according to claim 13, wherein an axis of each secondary wedging aperture (9, 10) is inclined in the direction of a proximal section (15) of said dental implant.

15. Dental implant according to claims 3, in which an attachment element of the proximal section (15) consists of a head (19) of polygonal cross-section.

* * * * *